United States Patent
Hirabuki

(10) Patent No.: US 9,060,920 B2
(45) Date of Patent: Jun. 23, 2015

(54) CLAMP AND BLOOD BAG SYSTEM

(71) Applicant: TERUMO KABUSHIKI KAISHA, Shibuya-ku (JP)

(72) Inventor: Makoto Hirabuki, Leuven (BE)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 13/722,447

(22) Filed: Dec. 20, 2012

(65) Prior Publication Data
US 2013/0123740 A1    May 16, 2013

Related U.S. Application Data

(63) Continuation of application No. PCT/JP2011/061768, filed on May 23, 2011.

(30) Foreign Application Priority Data

Jun. 30, 2010    (JP) ................................ 2010-149782

(51) Int. Cl.

| A61M 5/168 | (2006.01) |
|---|---|
| A61M 5/32 | (2006.01) |
| A61M 5/00 | (2006.01) |
| A61B 19/00 | (2006.01) |
| A61J 1/20 | (2006.01) |
| A61M 39/28 | (2006.01) |
| A61M 1/02 | (2006.01) |

(52) U.S. Cl.
CPC ............. *A61J 1/2089* (2013.01); *A61M 1/0209* (2013.01); *A61M 39/284* (2013.01)

(58) Field of Classification Search
CPC .......... A61B 19/00; A61M 5/32; A61M 5/00; A61M 5/168; A61J 1/2089
USPC .................................. 604/410, 403, 250, 409
See application file for complete search history.

(56) References Cited

U.S. PATENT DOCUMENTS

| 4,557,727 | A | * | 12/1985 | Handt | ............................. 604/80 |
| 2002/0087126 | A1 | * | 7/2002 | Quah | ............................ 604/250 |

(Continued)

FOREIGN PATENT DOCUMENTS

| JP | 2-004384 A | | 1/1990 | |
| JP | 02-4384 | * | 2/1990 | ............ A61M 5/168 |

(Continued)

OTHER PUBLICATIONS

International Search Report (PCT/ISA/210) issued on Aug. 16, 2011, by the Japanese Patent Office as the International Searching Authority for International Application No. PCT/JP2011/061768.

*Primary Examiner* — Tatyana Zalukaeva
*Assistant Examiner* — Sara Sass
(74) *Attorney, Agent, or Firm* — Buchanan Ingersoll & Rooney PC

(57) ABSTRACT

A clamp for a blood bag system includes a protrusion section which presses a tube, a locking section having a first engagement section and a second engagement section that form therebetween an engagement groove in which the protrusion section is positioned and by which engagement can be made, a first engagement release section which releases an engaged state between the first engagement section and the protrusion section; and a second engagement release section which releases an engaged state between the second engagement section and the protrusion section.

21 Claims, 11 Drawing Sheets

(56) References Cited

U.S. PATENT DOCUMENTS

2003/0146170 A1*  8/2003  Corbin et al. ................ 210/739
2010/0152681 A1*  6/2010  Mathias ....................... 604/250

FOREIGN PATENT DOCUMENTS

| JP | 2-17142 U | 2/1990 |
| JP | 5-277153 A | 10/1993 |

* cited by examiner

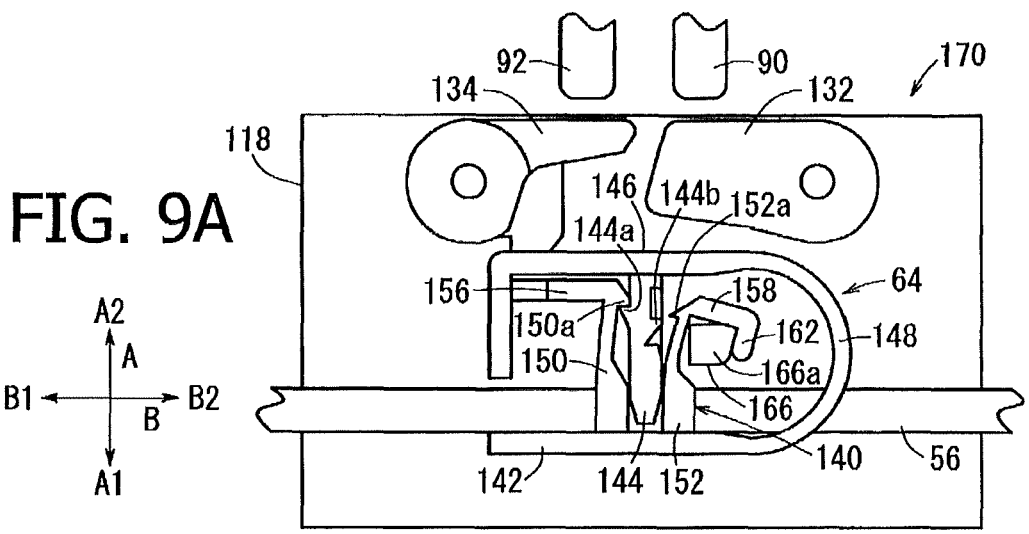
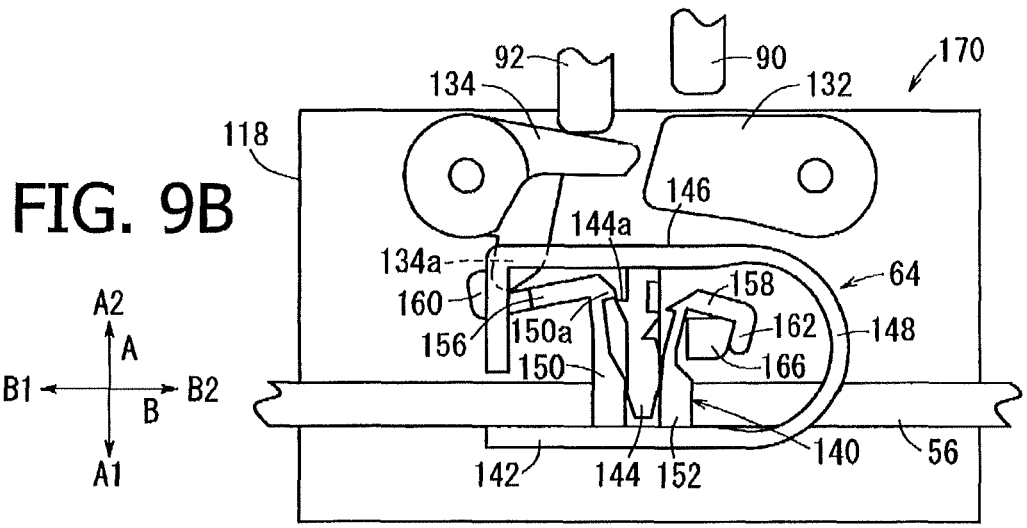
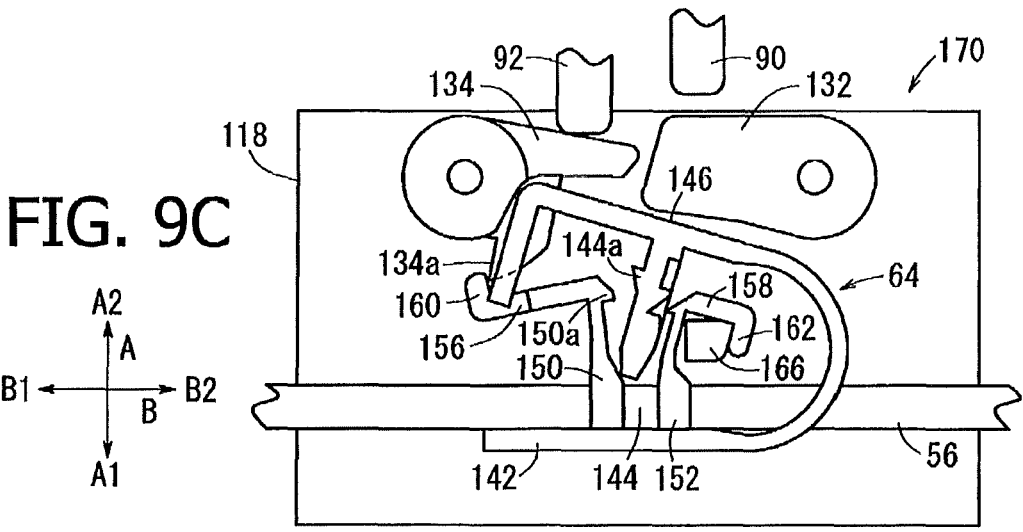

CLAMP AND BLOOD BAG SYSTEM

CROSS REFERENCES TO RELATED APPLICATIONS

This application is a continuation of International Application No. PCT/JP2011/061768 filed on May 23, 2011, and claims priority to Japanese Patent Application No. 2010-149782 filed in the Japanese Patent Office on Jun. 30, 2010, the entire content of both of which is incorporated herein by reference.

TECHNICAL FIELD

The present invention generally relates to a clamp which closes and opens a flow path in a tube and to a blood bag system having the clamp.

BACKGROUND DISCUSSION

In the past, whole blood transfusion in which all the components of blood obtained from blood donation are transfused has been the mainstream of blood transfusion. Recently, however, blood component transfusion has been practiced, attendant on the progress of technology, in which the blood obtained is separated into such components as red blood cells, platelets and plasma, and only the component or components needed by a patient are transfused. The blood component transfusion makes it possible to reduce the burden or side effects on the patient's circulatory system, while effectively utilizing the donated blood.

The blood (whole blood) obtained by blood donation, or a blood component prepared from the whole blood, is separated by centrifugation into a plurality of layers. For instance, when whole blood is centrifuged, the whole blood is separated into a light supernatant PPP (platelet poor plasma) fraction, a heavy precipitated CRC (concentrated red blood cells) fraction, and a buffy coat formed therebetween. When the buffy coat is centrifuged, it is separated into a supernatant component that contains platelets and leukocytes, and a precipitated component that contains red blood cells. When the residual component left after removal of leukocytes and platelets from whole blood is centrifuged, it is separated into a plasma layer as the supernatant component and a red blood cell layer as the precipitated component.

For separating whole blood into a plurality of blood components and containing and preserving the blood components in a plurality of preservation bags, or for further separating a blood component prepared from whole blood into a plurality of blood components and containing and preserving the blood components in a plurality of preservation bags, a blood bag system has been proposed in which a plurality of bags are interconnected by a plurality of tubes. An example of this blood bag system is described in U.S. Pat. No. 6,910,998. In such a blood bag system, for conducting predetermined blood treatments by switching over the communication states between the bags, clamps are provided for closing and opening the flow paths in the tubes. An example is disclosed in Japanese Patent Publication No. Hei 5-23792.

Such conventional clamps are each composed of a member possessing an overall flat C shape. The clamp includes a pair of pressing sections for pressing side surfaces of a tube, and an engagement section by which end portions of the C shape can be engaged with, and released from, each other. When the end portions are engaged with each other and the tube is pressed by the pair of pressing sections, the flow path in the tube is closed.

SUMMARY

In the above-mentioned blood treatment, the flow path in the tube is opened at the time when the component obtained by centrifugation of the blood component is transferred from a bag into another bag; in this case, the flow path in the tube must be securely closed at times other than the time of transfer. However, the conventional clamp has only one engagement section and, moreover, the engagement section can be easily operated by a finger of the person who handles the clamp. Therefore, even a light touch of a finger on the clamp may open the tube, which may influence the smoothness in carrying out the blood treatment.

The clamp disclosed here, and the disclosed blood system utilizing such clamp, can be opened and closed, and is configured so that the closed state of a tube can be maintained relatively assuredly and stably.

According to one aspect, a blood bag system comprises a plurality of bags each configured to contain whole blood or a blood component, at least one tube interconnecting the plurality of bags, and a clamp attached to the tube. The clamp comprises: a protrusion section configured to press the tube; a locking section having a first engagement portion configured to engage the protrusion section, a second engagement portion configured to engage the protrusion section, and an engagement groove located between the first engagement portion and the second engagement portion to receive the protrusion section; a first engagement release section which releases an engaged state between the first engagement portion and the protrusion section; and a second engagement release section which releases an engaged state between the second engagement portion and the protrusion section. The protrusion section is movable from a position in which the first engagement portion is in the engaged state with respect to the protrusion section so that the protrusion section is maintained at a position in contact with the tube to close a flow path through the tube, to a different position in which the engaged states of both the first engagement portion and the second engagement portion are released so that the protrusion section is spaced from the tube to open the flow path through the tube.

According to another aspect, a blood bag system comprises a first bag configured to contain a blood component, a second bag configured to contain a supernatant component obtained by centrifugation of the blood component, a third bag configured to contain a preservation liquid for preservation of a precipitated component obtained by centrifugation of the blood component, a transfer line interconnecting the first bag and the second bag, and interconnecting the first bag and the third bag, and having a branching section at an intermediate position of the transfer line, and a clamp attached to the transfer line at a position between the first bag and the branching section of the transfer line. The clamp comprises: a protrusion section configured to press the transfer line; a locking section having a first engagement portion configured to engage the protrusion section, a second engagement portion configured to engage the protrusion section, and an engagement groove located between the first engagement portion and the second engagement portion to receive the protrusion section; a first engagement release section which releases an engaged state between the first engagement portion and the protrusion section; and a second engagement release section which releases an engaged state between the second engagement portion and the protrusion section. The protrusion section is movable from a position in which the first engagement portion is in the engaged state with respect to the protrusion section so that the protrusion section is maintained at a position in contact with the transfer line to close a flow path through the transfer line, to a different position in which the engaged states of both the first engagement portion and the second engagement portion are released so that the protrusion section is spaced from the transfer line to open the flow path through the transfer line.

Another aspect of the disclosure involves a blood bag system comprising a plurality of bags each having an interior configured to contain whole blood or a blood component, a tube connecting the interior of one of the bags to the interior of an other of the bags, a clamp attached to the tube, a tube holder comprised of a tube guide passage in which at least a portion of the tube is positioned and a clamp holder located at intermediate portion of the tube guide passage, with the clamp being positioned in the clamp holder. The clamp which is positioned in the clamp holder comprises: an elongated protrusion section movable into contact with the tube to close a flow passage in the tube and movable away from the tube to open the flow passage; an elongated first engagement portion engageable with one part of the protrusion section in an engaged state of the first engagement portion to hold the protrusion section at a position at which the protrusion section is in contact with the tube and closes the flow passage in the tube, with the first engagement portion being movable from the engaged state to a disengaged state of the first engagement portion in which the first engagement portion is out of engagement with the one part of the protrusion section; and a first engagement release section which releases the engaged state between the first engagement portion and the one part of the protrusion section to move the first engagement portion to the disengaged state of the first engagement portion. The protrusion section is held in contact with the tube to close the flow passage in the tube in the engaged state of the first engagement portion and is movable out of contact with the tube to open the flow passage when the first engagement portion is in the disengaged state.

Another aspect involves a clamp for closing and opening a flow path in a tube. The clamp comprises: a protrusion section configured to press the tube: a locking section having a first engagement portion configured to engage the protrusion section, a second engagement portion configured to engage the protrusion section, and an engagement groove located between the first engagement portion and the second engagement portion to receive the protrusion section; a first engagement release section which releases an engaged state between the first engagement portion and the protrusion section; and a second engagement release section which releases an engaged state between the second engagement portion and the protrusion section. The protrusion section is movable from a position in which the first engagement portion is in the engaged state with respect to the protrusion section so that the protrusion section is maintained at a position in contact with the tube to close a flow path through the tube, to a different position in which the engaged states of both the first engagement portion and the second engagement portion are released so that the protrusion section is spaced from the tube to open the flow path through the tube.

The lock of the protrusion section by the locking section is preferably not released unless both the engagement of the first engagement release section and the engagement of the second engagement release section are released. Therefore, a closed state of the tube can be maintained relatively reliably and stably.

The clamp preferably has a configuration that includes, integrally formed, a base section with the locking section erected, an opening/closing section with the protrusion section erected, and a bent section interconnecting the base section and the opening/closing section so that the base section and the opening/closing section are opposed to each other. The first engagement section and the second engagement section are preferably disposed in this order along the direction from a tip of the base section toward the bent section side; and the second engagement release section is located between the protrusion section and the bent section in a condition where the protrusion section and the locking section are engaged with each other.

The second engagement release section is thus located in such a position as to be difficult to operate by a finger of the person who handles the clamp. Therefore, the closed state of the tube can be maintained further assuredly.

The clamp is preferably configured so that the second engagement release section projects from the second engagement section toward the bent section side, and a hook piece with which a release pin for putting the second engagement release section into a releasing state can be engaged is provided at a tip of the second engagement release section.

Engagement of the hook piece with the release pin puts the second engagement release section into the releasing state. Therefore, the second engagement release section can be rather smoothly put into the releasing state by an action of the hook piece.

The first engagement release section preferably projects from the first engagement section in a direction for spacing away from the second engagement section, and is located between the base section and the opening/closing section in a condition where the protrusion section and the locking section are engaged with each other.

The first engagement release section is thus located in such a position as to be difficult to be (inadvertently) operated by a finger of the person who handles the clamp. This helps ensure that the closed state of the tube can be maintained further reliably.

The opening/closing section is preferably configured to include an opening section which partly exposes the first engagement release section so that the first engagement release section can be pressed from outside of the opening/closing section.

The first engagement release section can thus be pressed from outside of the opening/closing section, through the opening section. Therefore, even in the case where means for operating the first engagement release section is provided at a position outside of the first engagement release section, the first engagement release section can be easily put into a releasing state.

In the blood bag system, the clamp which can stably maintain the locking state and can be opened when necessary is attached to the tube. Therefore, it is possible, by opening and closing the flow path in the tube interconnecting the bags, to switch over the communication states between the bags and to suitably perform desired blood treatments.

BRIEF DESCRIPTION OF DRAWINGS

FIG. 9A is a view showing a condition wherein the clamp is closed to close the tube, FIG. 9B is a view showing a condition wherein engagement of a first engagement section is released, and FIG. 9C is a view showing a condition in which the clamp is opened by release of engagement of the first engagement section.

DETAILED DESCRIPTION

A clamp, and a blood bag system utilizing such clamp, is described below with reference to the accompanying drawings.

Figure 1:
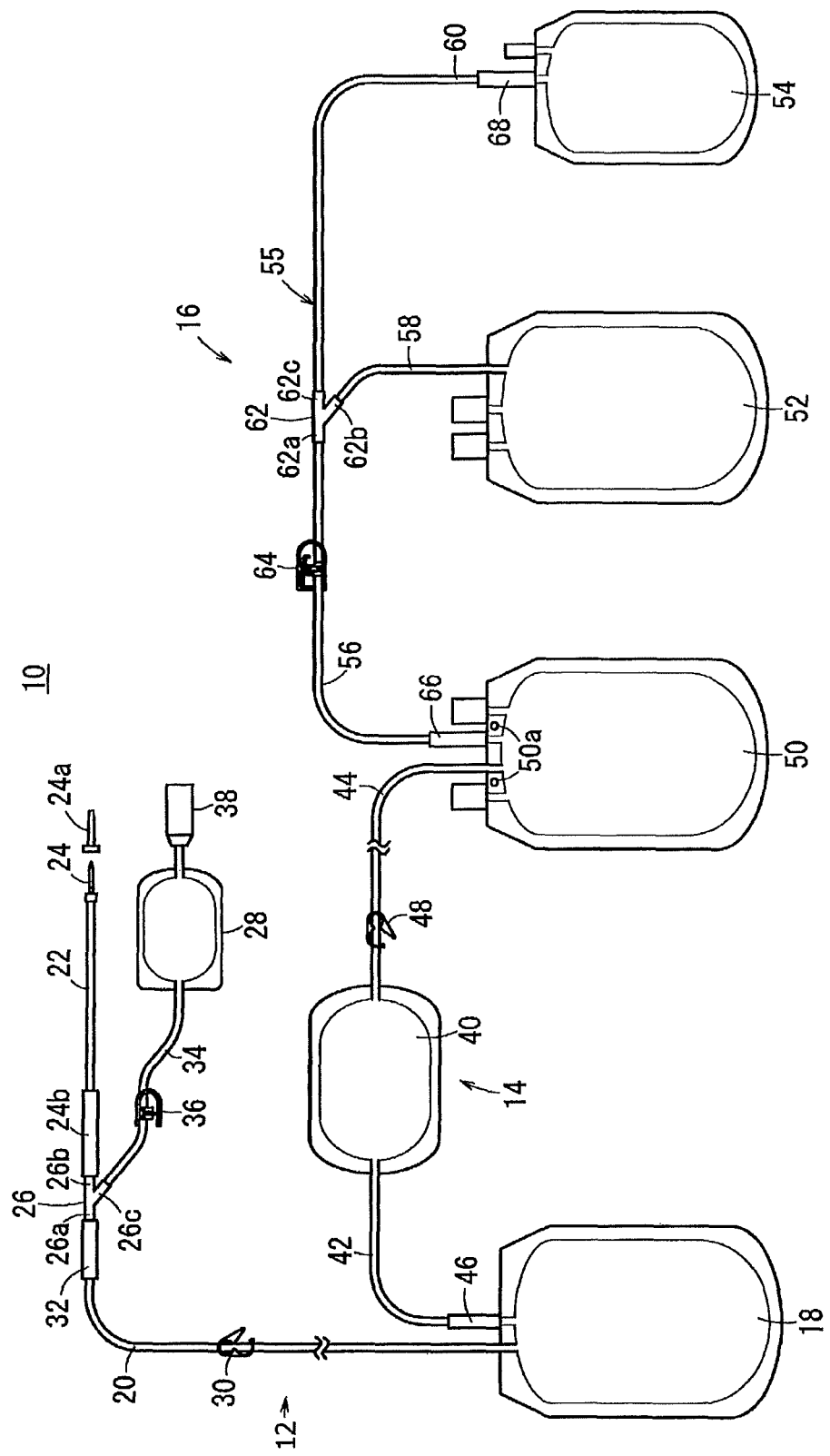
FIG. 1 is a plan view of a blood bag system according to one embodiment disclosed here.

FIG. 1 is a plan view of a blood bag system 10 according to one embodiment of the present invention. The blood bag system 10 is for centrifuging blood containing a plurality of components into a plurality of components differing in specific gravity (for example, three components including a low specific gravity component, an intermediate specific gravity component and a high specific gravity component, or two components including a low specific gravity component and a high specific gravity component) and containing and preserving the components separately in different bags. The blood bag system 10 according to this embodiment is configured to centrifuge a residual blood component, obtained by removing leukocytes and platelets from whole blood, into two components including plasma and concentrated red blood cells, and to contain and preserve the plasma and the concentrated red blood cells separately in different bags.

The blood bag system 10 includes a blood collection section 12 for collection of blood (whole blood) from a donor, a pretreatment section 14 for removing a predetermined blood component from the whole blood, and a separating treatment section 16 by which the residual blood component obtained upon removal of the predetermined component is centrifuged into a plurality of blood components and the blood components are contained (reserved) in different bags.

First, the blood collection section 12 will be described. The blood collection section 12 includes a blood collection bag 18, first and second blood collection tubes 20 and 22, a blood collection needle 24, a branching connector 26, and a first flow blood bag 28.

The blood collection bag 18 is a bag for containing (reserving) the blood (whole blood) collected from the donor. Preferably, an anticoagulant is preliminarily placed in the blood collection bag 18. The anticoagulant is normally a liquid, and examples thereof include ACD-A liquid, CPD liquid, CPDA-1 liquid, and heparin sodium liquid. The amount of these anticoagulants is an appropriate amount according to the amount of blood to be collected.

The blood collection bag 18 is configured in a bag form by a method involving, for example, laying flexible sheet materials made of a flexible resin such as polyvinyl chloride or polyolefin on each other, and welding the sheet materials (e.g., by thermal fusion bonding or high-frequency fusion bonding) or adhering the sheet materials to each other in a peripheral sealing area. The first flow blood bag 28 is also configured in a bag form.

One end of the first blood collection tube 20 (proximal-side blood collection tube) is connected to an upper portion of the blood collection bag 18. At an intermediate portion of the first blood collection tube 20 is provided a clamp 30 for closing and opening a flow path in the first blood collection tube 20. The clamp 30 is a resin-made member formed in a flat C shape as a whole. The clamp 30 includes a pair of pressing sections which press side surfaces of the first blood collection tube 20, and an engagement section so configured that end portions of the C shape can be thereby engaged with each other and the engagement can be thereby released. When the end portions are engaged with each other and the first blood collection tube 20 is pressed by the pair of pressing sections, the flow path in the first blood collection tube 20 is closed.

To the other end of the first blood collection tube 20 is connected one end of a breakable sealing member (breakable communication member) 32. The sealing member 32 is so configured that a flow path therein is closed in an initial state and that the flow path is opened by a breaking operation.

Such a sealing member 32 includes a tube formed from a flexible resin such as polyvinyl chloride, and a tubular body which is connected liquid-tight in the tube, is closed at one end thereof, and is provided with a brittle part at a longitudinal-directionally one portion thereof. In order to put the sealing member 32 into an open state, the tubular body is bent by fingers or the like from outside of the tube, thereby breaking the brittle part. As a result, the flow path in the tube which has been closed with the tubular body is opened, and the sealing member 32 is put into the open state.

To the other end of the sealing member 32 is connected a first port 26a of the branching connector 26. To a second port 26b of the branching connector 26 is connected one end of the second blood collection tube (distal-side blood collection tube) 22, and to the other end of the second blood collection tube 22 is connected the blood collection needle 24. Until the system is put to use, a cap 24a is kept attached to the blood collection needle 24, and, after use, a needle guard 24b is attached to the blood collection needle 24. The needle guard 24b is so disposed as to be movable along the longitudinal direction of the second blood collection tube 22.

To a third port 26c of the branching connector 26 is connected one end of a branch tube 34. At an intermediate portion of the branch tube 34 is provided a clamp 36 which closes and opens a flow path in the branch tube 34. The clamp 36 is so configured that once it is closed, it cannot be opened. An example of a clamp which can be used as the clamp 36 is the clamp disclosed in Japanese Patent Publication No. Hei 5-23792 can be used.

To the other end of the branch tube 34 is connected the first flow blood bag 28. At the time of collecting blood from a donor, before collecting the blood into the blood collection bag 18, first, a predetermined amount of a first flow of the blood collected (blood collection first flow) is contained or collected into the first flow blood bag 28. In this case, while keeping the sealing member 32 in a closed state (initial state), the clamp 36 is put into an open state. This helps ensure that flow of the blood collection first flow to the first blood collection tube 20 side, namely, to the blood collection bag 18 side is inhibited, and, on the other hand, the blood collection first flow can be introduced through the second blood collection tube 22, the branching connector 26 and the branch tube 34 into the first flow blood bag 28.

To the first flow blood bag 28 is connected a sampling port 38. A blood collection tube is attached to the sampling port 38, whereby the blood collection first flow is collected into the blood collection tube. The blood collection first flow thus collected serves as a test blood. The portion ranging from the branching connector 26 to the sampling port 38 may be omitted, depending on use.

The pretreatment section 14 includes a filter 40 for removing predetermined cells, an inlet-side tube 42 connected at its one end to the blood collection bag 18 and at its other end to an inlet of the filter 40, and an outlet-side tube 44 connected at its one end to an outlet of the filter 40 and at its other end to the separating treatment section 16.

In this embodiment, the filter 40 is configured as a leukocyte removing filter. As the leukocyte removing filter, there can be used a filter having a structure wherein a liquid-passing porous body having a multiplicity of micropores communicating from one side surface to the other side surface thereof is contained in a bag-formed housing formed from a flexible resin sheet. In this embodiment, the filter 40 is so configured as to be capable of trapping platelets, as well.

The inlet-side tube 42 is a tube through which the blood collected from a donor is transferred from the blood collection bag 18 to the filter 40, and which is connected to an upper portion of the blood collection bag 18. In this embodiment, a sealing member 46 is provided at that end of the inlet-side tube 42 which is located on the blood collection bag 18 side. The sealing member 46 has the same or similar configuration and function to those of the above-described sealing member 32.

The outlet-side tube 44 is a tube through which the residual blood component obtained upon removal of predetermined cells (in this embodiment, leukocytes and platelets) by the filter 40 is transferred to the separating treatment section 16 (specifically, a primary bag 50 which will be described later). A clamp 48 is provided at an intermediate portion of the outlet-side tube 44, and the clamp 48 closes and opens a flow path in the outlet-side tube 44. The clamp used as the clamp 48 can be the same as the above-described clamp 30.

The separating treatment section 16 will now be described below. The separating treatment section 16 includes the primary bag (first bag) 50 for containing (reserving) the residual blood component obtained upon removal of the predetermined cells by the filter 40, a sub bag (second bag) 52 for containing and preserving a supernatant component obtained by centrifugation of the blood component contained in the primary bag 50, an additive solution bag (third bag) 54 for containing a red blood cell preservation liquid, and a transfer line 55 which is connected to the primary bag 50, the sub bag 52 and the additive solution bag 54.

The primary bag 50, the sub bag 52 and the additive solution bag 54 are each configured in a bag form by a method in which, for example, flexible sheet materials formed from a flexible resin such as polyvinyl chloride or polyolefin are welded (e.g., by thermal fusion bonding or high-frequency fusion bonding) to each other in a peripheral sealing area, like the blood collection bag 18.

The primary bag 50 serves as both a bag for containing (reserving) the residual blood component obtained upon removal of the predetermined cells by the filter 40 and a bag for preserving a precipitated component (concentrated red blood cells) obtained by centrifugation of the residual blood component.

The transfer line 55, which includes a branching connector (branching section) 62 at an intermediate position thereof, interconnects the primary bag 50 and the sub bag 52, and interconnects the primary bag 50 and the additive solution bag 54. In the example shown, the transfer line 55 includes a first tube 56 connected to the primary bag 50, a second tube 58 connected to the sub bag 52, a third tube 60 connected to the additive solution bag 54, the branching connector 62 connected to the first, second and third tubes 56, 58, 60, and an openable and closable clamp 64 attached to the first tube 56.

A breakable sealing member 66 is provided at one end portion (end portion on the primary bag 50 side) of the first tube 56, whereby transfer of the blood component in the primary bag 50 into other bag is prevented until a breaking operation is conducted. The sealing member 66 has the same or similar configuration and function to those of the above-mentioned sealing member 32.

The other end portion of the first tube 56 is connected with a first port 62a of the branching connector 62. To a second port 62b of the branching connector 62 is connected one end of the second tube 58. To a third port 62c of the branching connector 62 is connected one end of the third tube 60.

The clamp 64 is attached to an intermediate portion of the first tube 56, and is configured to close and open a flow path in the first tube 56. A more detailed discussion of the clamp 64 will be set forth later.

The red blood cell preservation liquid contained in the additive solution bag 54 can be a MAP liquid, a SAGM liquid, an OPTISOL or the like. A breakable sealing member 68 is provided at an end portion on the additive solution bag 54 side of the third tube 60, whereby the red blood cell preservation liquid in the additive solution bag 54 is prevented from being transferred into another bag. The sealing member 68 has the same or similar configuration and function as those of the above-described sealing member 32.

Each tube in the blood bag system 10 is a tube made of a transparent flexible resin. The clamps 30, 36, 48 may be known products which have previously been used. The clamps 30, 36, 48, 64 are preferably colored differently, depending on the area and/or purpose of use. At the time of sterilization of the blood bag system 10 and during storage of the blood bag system 10 before use, the clamps 30, 36, 48, 64 are in an open state and, therefore, the inside of the bags is in communication and in a uniform sterilized state.

Figure 2:
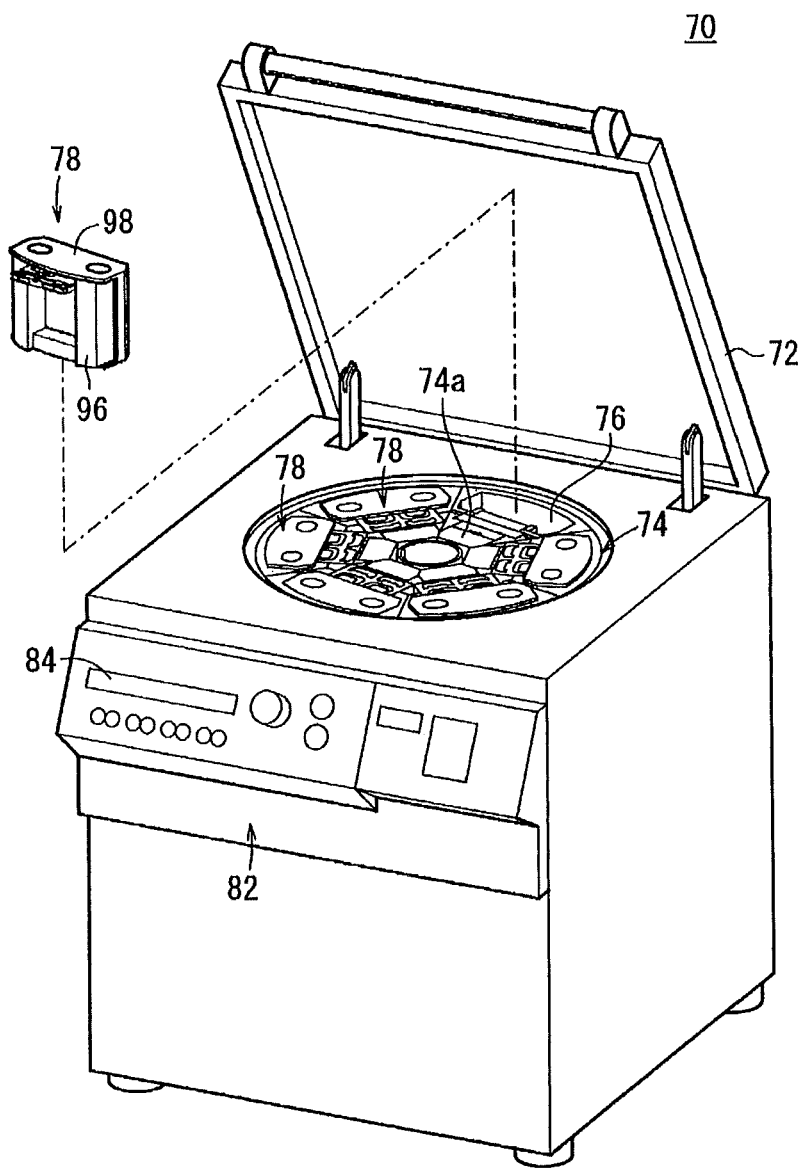
FIG. 2 is a perspective view of a centrifuge and transfer apparatus.

The blood bag system 10 according to this embodiment can be used, for example, in the state of being mounted in a centrifuge and transfer apparatus 70 shown in FIG. 2. The centrifuge and transfer apparatus 70 is used for centrifuging the blood component contained in the primary bag 50 into two layers including a plasma layer and a concentrated red blood cell layer, and transferring the plasma into the sub bag 52, while leaving the concentrated red blood cells in the primary bag 50.

To help facilitate an understanding of the method of using the blood bag system 10, the configuration of the centrifuge and transfer apparatus 70 will be described below. In the following description, the direction indicated by the arrows A in FIG. 3 will be referred to as radial direction, and the direction indicated by the arrows B will be referred to as the circumferential direction. While the circumferential direction is strictly the direction along the circular arc like arrows B, the direction orthogonal to arrow A will also be referred to as the circumferential direction in paragraphs of the description thereof, for convenience of description.

As shown in FIG. 2, the centrifuge and transfer apparatus 70 is box-shaped as a whole, and includes: an openable and closable lid 72 on the upper side; a centrifugal drum (centrifuging means) 74 inside; six unit insertion holes 76 arranged in regular angular intervals (60 degrees) inside the centrifugal drum 74; six insert units 78 inserted respectively in the unit insertion holes 76; and six pushers (pressing means) 80 (see FIG. 3) which are each provided in a central area and can be advanced and retracted in the rotational radial direction relative to each of the insert units 78. The centrifuge and transfer apparatus 70 is operated based on an operation of an operating section 82 provided at the front of the apparatus, is controlled by a microcomputer, and can display predetermined information on a monitor 84.

Figure 3:
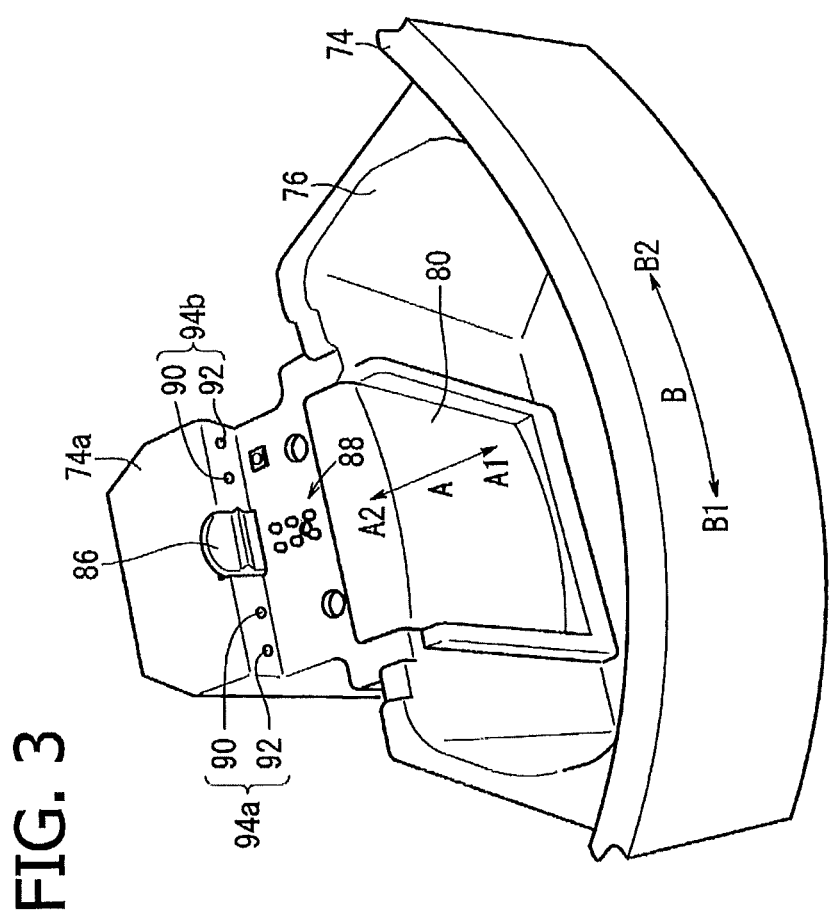
FIG. 3 is a partly enlarged perspective view of a centrifugal drum in the centrifuge and transfer apparatus.

As shown in FIG. 3, a central body 74a of the centrifugal drum 74 has a holding lever 86, electrodes 88, first rods 90 and second rods 92, and the pushers 80. The first rods 90 and the second rods 92 are each driven to advance and retract in the radial direction A, and they are provided in two pairs as illustrated in FIG. 3. In this embodiment, the first rod 90 and the second rod 92 on the first circumferential direction B1 side constitute an example of clamp driving means 94a for opening and closing the clamp 64 (see FIG. 1). The part shown in FIG. 3 may be configured as one unit, and six such units may be combined with one another and arranged in the circumferential direction.

The centrifuge and transfer apparatus 70 can also be used for centrifuging whole blood into three layers, including a plasma layer, a buffy coat layer and a concentrated red blood cell layer, and transferring the thus obtained blood components into other bags. In that case, for centrifugation and transfer, opening and closing operations must be applied to each of the two clamps. In such a case, therefore, the first rod 90 and the second rod 92 on the second circumferential direction B2 side function as an example of second clamp driving means 94b for opening and closing the clamps.

Figure 4:
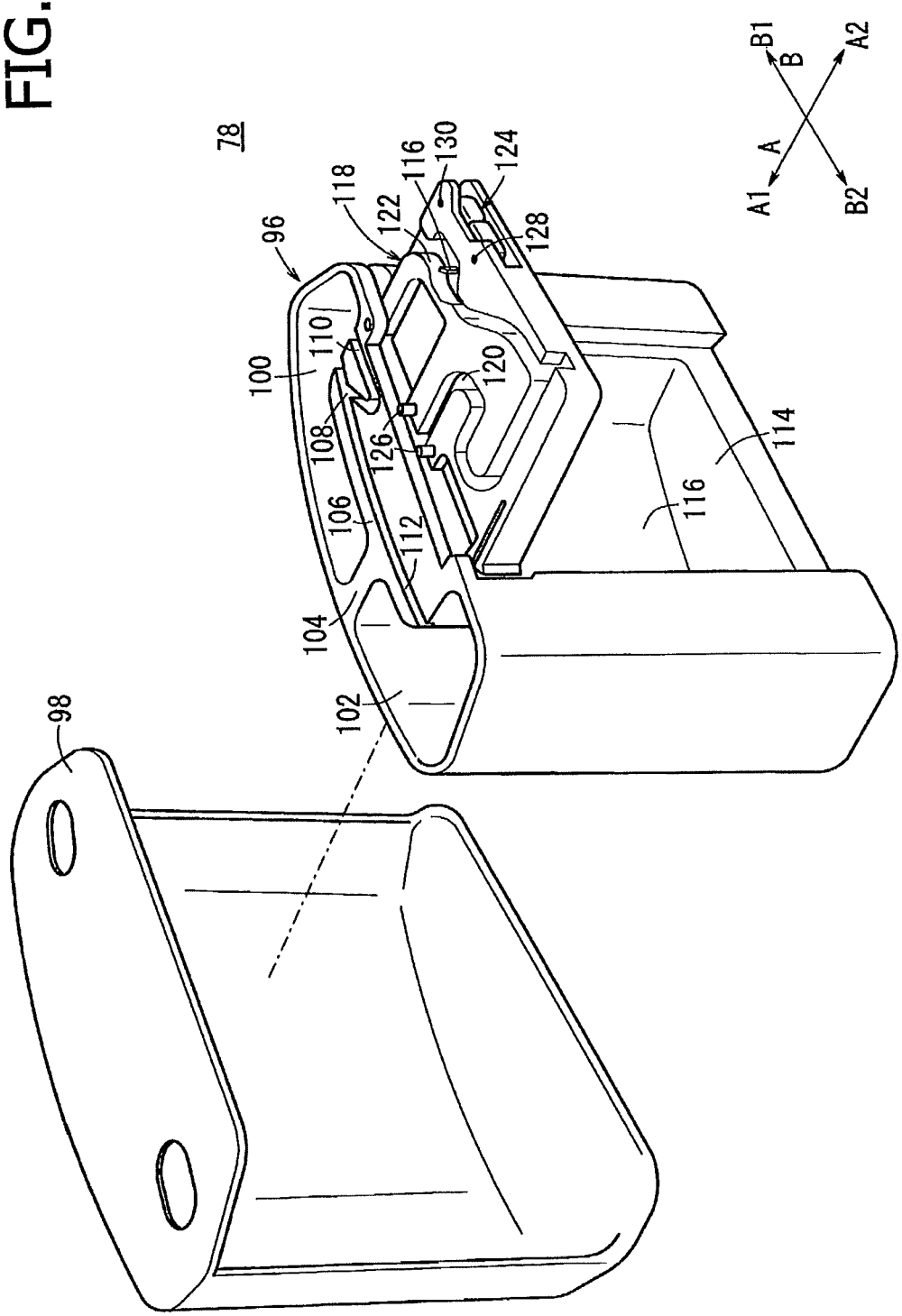
FIG. 4 is an exploded perspective view of an insert unit.

FIG. 4 is an exploded perspective view of the insert unit 78 as viewed from the radially inner side (inward radial direction A2). As shown in FIG. 4, the insert unit 78 has a unit body 96, and a cover body 98. The unit body 96 is a bottomed tube having a relatively wide circular arc-shaped in top view and is open on the upper side, wherein a first chamber 100 on the B1 direction side and a second chamber 102 on the B2 direction side are partitioned from each other by a wall 104 extending in the A direction.

The unit body 96 is provided with an upper wall 106 on the radially inner side in an upper portion of the unity body 96. The upper wall 106 is formed with: a connector mounting groove 108 for mounting the branching connector 62 therein; a first guide groove 110 for guiding a part, on the branching connector 62 side, of the second tube 58; and a second guide groove 112 for guiding a part, on the branching connector 62 side, of the third tube 60.

Under the upper wall 106 is provided a third chamber 114, which opens in the A2 direction. The third chamber 114 is partitioned from the first chamber 100 and the second chamber 102 by a wall 116 extending in the B direction. In addition, the unit body 96 is provided at its upper portion with a plate-shaped tube holder 118 which projects toward the radially inner side. The above-mentioned holding lever 86 (see FIG. 3) is elastically biased, and holds the tube holder 118. The tube holder 118 has a tube guide passage 120 for guiding the first tube 56, and two pins 126, 126 provided at its end portion in the outward radial direction A1. The tube guide passage 120 is in the shape of a groove which is formed by walls on both sides of the passage along roughly the whole length of the passage, and is open on the upper side.

The tube guide passage 120 extends in the inward radial direction A2 from the vicinity of the center of an end portion with respect to the outward radial direction A1 of the tube holder 118, is then bent in a reverse S pattern at an intermediate portion with respect to the radial direction A, and is bent in the vicinity of an end portion with respect to the inward radial direction A2 to extend in the B1 direction, until it reaches an end portion with respect to the B1 direction of the tube holder 118. The tube guide passage 120 is provided, at a portion forming a groove in the circumferential direction B, with a clamp holding section 122 for holding the above-mentioned clamp 64. The tube holder 118 further has a clamp operating section 124 for operating of shifting the clamp 64 between a closed state and an open state.

The cover body 98 is a cover which is mounted to the unit body 96 from outside. The cover body 98 can cover an outside surface, an upper surface and a lower surface of the unit body 96, and can assuredly hold the blood bag system 10 mounted in the unit body 96.

Figure 5:
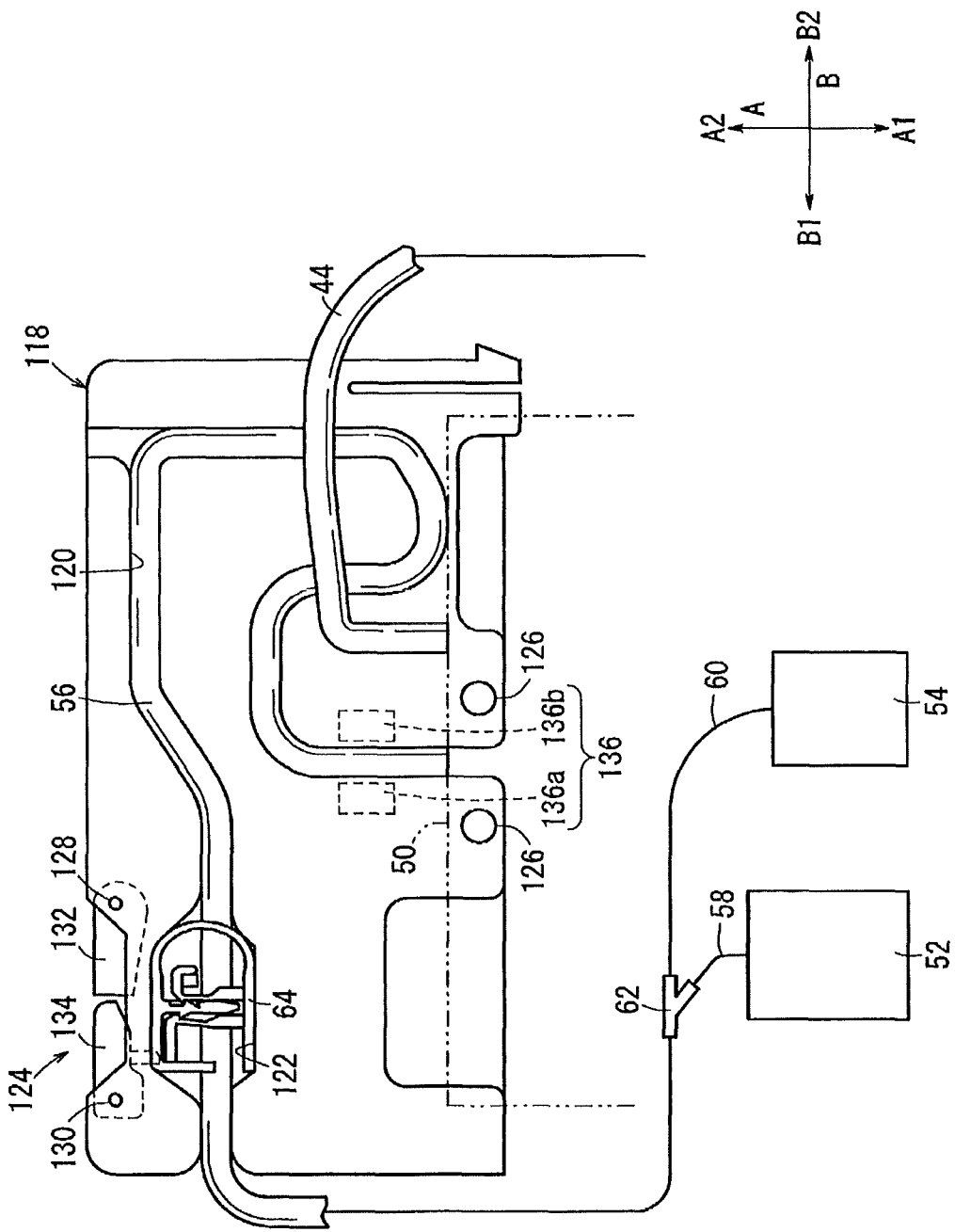
FIG. 5 is a schematic illustration of a condition wherein a tube in the blood bag system according to the one embodiment is held by a tube holder of the centrifuge and transfer apparatus.

FIG. 5 is a schematic illustration of a condition where the first tube 56 and the clamp 64 are held by the tube holder 118. In FIG. 5, for facilitating an easier understanding, a part of the primary bag 50 with an upper portion fixed by the two pins 126, 126 of the tube holder 118 is indicated by imaginary lines. In addition, parts of the first tube 56 and the outlet-side tube 44, the second tube 58, the third tube 60, the sub bag 52 and the additive solution bag 54 are shown in simplified form.

As shown in FIG. 5, the primary bag 50 has its upper portion fixed to the tube holder 118 by a method in which the two pins 126, 126 provided in the tube holder 118 are inserted into two holes 50a, 50a (see FIG. 1) provided at the upper portion of the primary bag 50. The first tube 56 is mounted in the tube guide passage 120 of the tube holder 118, so that the first tube 56 is held. In addition, the clamp 64 provided on the first tube 56 is held by the clamp holding section 122. The sub bag 52 connected to the second tube 58 is contained in the first chamber 100 (see FIG. 4). The additive solution bag 54 connected to the third tube 60 is contained in the second chamber 102 (see FIG. 4).

After the residual blood component obtained upon filtration of whole blood by the filter 40 is transferred to and contained in the primary bag 50, and before the blood bag system 10 is mounted in the centrifuge and transfer apparatus 70, the outlet-side tube 44 is subjected to fusion bonding by a tube sealer or the like to be thereby sealed in a leak-preventive manner, before being cut. Therefore, with respect to the blood bag system 10, only the separating treatment section 16 and a part of the outlet-side tube 44 are mounted to the unit body 96.

The clamp 64 is opened and closed by being operated by the clamp operating section 124 provided in the tube holder 118. The clamp operating section 124 has a first pressing element 132 and a second pressing element 134 which are turnable about the pins 128, 130 respectively. The clamp operating section 124 is so configured that the clamp 64 is closed when the clamp 64 is pressed by the first pressing element 132 and that the clamp 64 is opened when the clamp 64 is pressed by the second pressing element 134. The operations of opening and closing the clamp 64 by the clamp operating section 124 will be described in more detail later.

As shown in FIG. 5, the tube holder 118 further has a sensor 136 by which the kind of a liquid passing through the first tube 56 is detected at a position upstream of the clamp 64. The sensor 136 includes a light casting section 136a and a light receiving section 136b, and can determine the kind of a liquid passing between the two sections 136a, 136b on the basis of the degree of transmission of light through the liquid. The tube holder 118 is provided at its lower surface with a plurality of contacts for electrical continuity with the sensor 136 or an interface circuit of the sensor. These contacts are put into contact with the reception-side electrodes 88 (see FIG. 3)

provided on the central body 74a of the centrifugal drum 74, whereby a signal from the sensor 136 is supplied to the microcomputer.

The blood bag system 10 according to this embodiment is fundamentally configured as above-described, and its operation and effect will now be described below.

Reference is initially made to FIG. 1. In collecting blood from a donor, as above-described, first, the blood collection first flow is collected into the first flow blood bag 28. After collection of the blood collection first flow is completed, the branch tube 34 is closed by the clamp 36, and the above-mentioned breaking operation is applied to the sealing member 32 to open the flow path in the first blood collection tube 20. In this instance, the clamp 30 is set in the open state, whereas the sealing member 46 is set in the initial state (closed state). As a result, the blood from the donor flows through the second and first blood collection tubes 22 20 into the blood collection bag 18. After a predetermined amount of blood is collected into and reserved in the blood collection bag 18, the first blood collection tube 20 is closed by the clamp 30 so that the blood (whole blood) in the blood collection bag 18 is not able to flow out. Then, the first blood collection tube 20 is subjected to fusion bonding and sealing by a tube sealer or the like, after which the second blood collection tube 22 is cut at the sealed portion.

Next, the blood collection bag 18 is put in an upper position, while the primary bag 50 is put in a lower position, and the filter 40 is disposed in an intermediate position. Thereafter, a breaking operation is applied to the sealing member 46 at one end portion of the inlet-side tube 42 to open a flow path in the inlet-side tube 42. This results in the whole blood in the blood collection bag 18 flowing through the inlet-side tube 42 into the filter 40, whereby leukocytes and platelets are removed during passage of the whole blood through the filter 40, and the residual blood component flowing through the outlet-side tube 44 into the primary bag 50, thereby being collected. Thereafter, the outlet-side tube 44 is subjected to fusion bonding and sealing at a position downstream of the clamp 48, followed by cutting the outlet-side tube 44 at the sealed portion.

Subsequently, in order to separate the blood component collected into the primary bag 50 into plasma and concentrated red blood cells, and reserving the plasma and the concentrated red blood cells respectively into predetermined bags, the separating treatment section 16 of the blood bag system 10 is mounted into the centrifuge and transfer apparatus 70. In this mounting, first, the flow path in the first tube 56 is put into a closed state by the clamp 64, after which the above-mentioned breaking operation is applied to the sealing member 66, to open the flow path therein.

Then, as shown in FIG. 5, the first tube 56 is held by the tube holder 118, and the primary bag 50 is contained into (positioned in) the third chamber 114 (see FIG. 4) of the unit body 96, with its upper portion fixed to the tube holder 118. In addition, the sub bag 52 is contained into (positioned in) the first chamber 100, and the additive solution bag 54 is contained into (positioned in) the second chamber 102. In this instance, the sub bag 52 is preferably contained in the first chamber 100 in a non-folded state so that in a separating step after a centrifuging step, the plasma flows rather smoothly into the sub bag 52, to be preserved there. After the separating treatment section 16 is mounted to and contained in the unit body 96, the cover body 98 is mounted to the unit body 96, thereby putting the insert unit 78 into an assembled state.

Next, as shown in FIG. 2, the insert unit 78 with the blood bag system 10 contained therein is inserted into the unit insertion hole 76 of the centrifuge and transfer apparatus 70.

As a result, the holding lever 86 fixes an end portion of the tube holder 118. In addition, contacts of the sensor or the interface circuit thereof come into contact with the electrodes 88 (see FIG. 3). While six insert units 78 are preferably mounted into the centrifuge and transfer apparatus 70, five or less insert units (preferably, three or two insert units arranged at regular angular intervals) may be mounted, insofar as the insert units are well-balanced.

Subsequently, the lid 72 of the centrifuge and transfer apparatus 70 is closed, and the centrifuging step and the separating step are automatically conducted by operating the operating section 82. In the automatic operation of the centrifuge and transfer apparatus 70, first, the centrifuging step is carried out by rotating the centrifugal drum 74. In this instance, the clamp 64 is preliminarily closed. To help ensure assured closure, it is preferable to once advance the first rod 90 so as to put the clamp 64 into the closed state.

Figure 6:
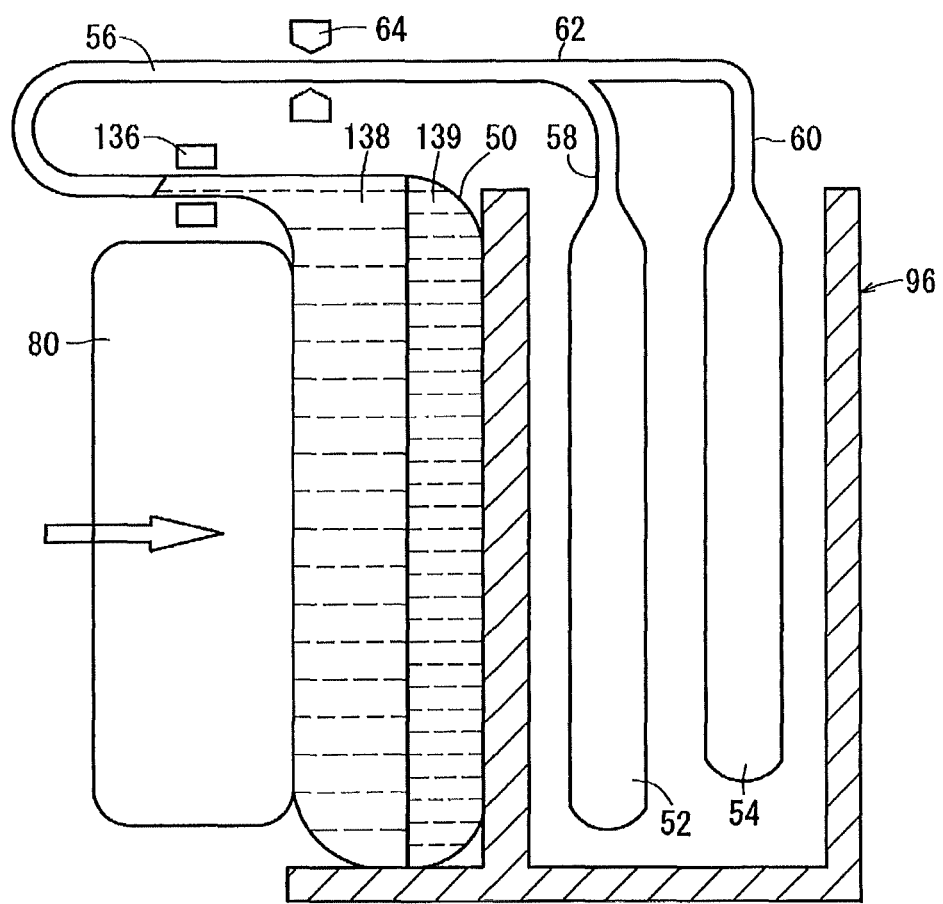
FIG. 6 is an illustration of an operation in the centrifuge and transfer apparatus.

As shown in FIG. 6, in the centrifuging step, the blood component reserved in the primary bag 50 in the first chamber 100 receives a centrifugal force. This results in the concentrated red blood cells 139 as a high specific gravity component are transferred in the outward radial direction, whereas the plasma 138 as the low specific gravity component is transferred in the inward radial direction, whereby the blood component is separated into two layers.

The centrifuge and transfer apparatus 70 proceeds to the separating step after the centrifuging step. In the separating step, with the centrifugal drum 74 kept rotating, the second rod 92 of the clamp driving means 94a is operated to put the flow path in the first tube 56 into an open state.

Next, as shown in FIG. 6, the pusher 80 is displaced in the centrifugal direction A1 so as to press the primary bag 50. The primary bag 50 is reduced in internal volume by being clamped between the pusher 80 and the wall, and the liquid contained in the primary bag 50 is thus discharged via the first tube 56. In this instance, since the first tube 56 is directed toward the radially inner side, the plasma 138 located on the most inner side in the radial direction flows out of the primary bag 50, and flows through the first tube 56, the branching connector 62 and the second tube 58 into the sub bag 52.

After the plasma 138 finishes flowing out of the primary bag 50, the concentrated red blood cells 139 start flowing out of the primary bag 50. In this instance, when the flow of the red blood cells through the first tube 56 is detected by the sensor 136 (see FIG. 5, as well), the pusher 80 is stopped, and the first rod 90 of the clamp driving means 94a is operated to close the flow path in the first tube 56 by the clamp 64. As a result, the red blood cells are inhibited from flowing into the sub bag 52. The sensor 136 can confirm the flow of the red blood cells through the first tube 56, based on the transparency (in other words, turbidity) of the liquid flowing through the first tube 56.

When the separating step as above-described is finished, the separating treatment section 16 is taken out of the insert unit 78, then the second tube 58 is subjected to fusion bonding and sealing, and is thereafter cut, whereby the sub bag 52 is separated off. Next, with the additive solution bag 54 disposed in an upper position and with the primary bag 50 disposed in a lower position, the clamp 64 is operated to open the flow path in the first tube 56, whereby the red blood cell preservation liquid in the additive solution bag 54 is permitted to flow through the third tube 60 and the first tube 56 into the primary bag 50. When it is confirmed that the discharge of the red blood cell preservation liquid from the additive solution bag 54 has been conducted sufficiently, the first tube 56 is subjected to fusion bonding and sealing, and is then cut, whereby the primary bag 50 is separated off.

By carrying out the above-mentioned treatments, it is possible to remove leukocytes and platelets from the whole blood, separating the residual blood component into two components including the plasma and the concentrated red blood cells, and to separately contain the plasma and the concentrated red blood cells into different bags (the primary bag 50 and the sub bag 52) for preserving them.

Figure 7A:
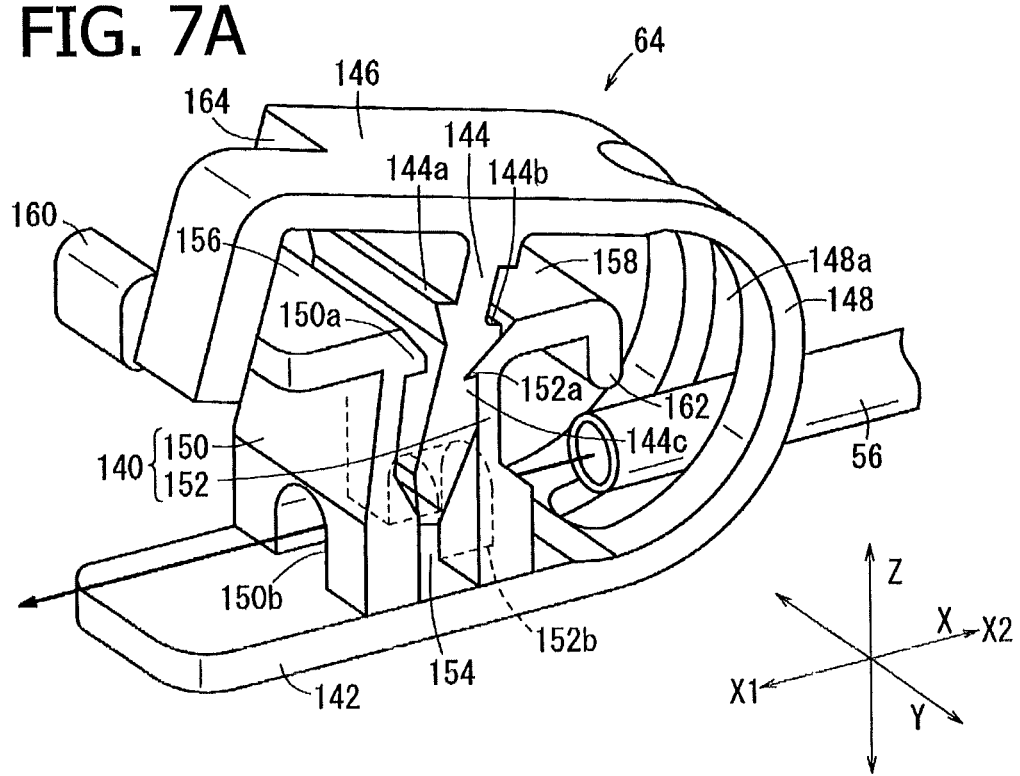
FIG. 7A is a perspective view of a clamp in a prelocking state.
Figure 7B:
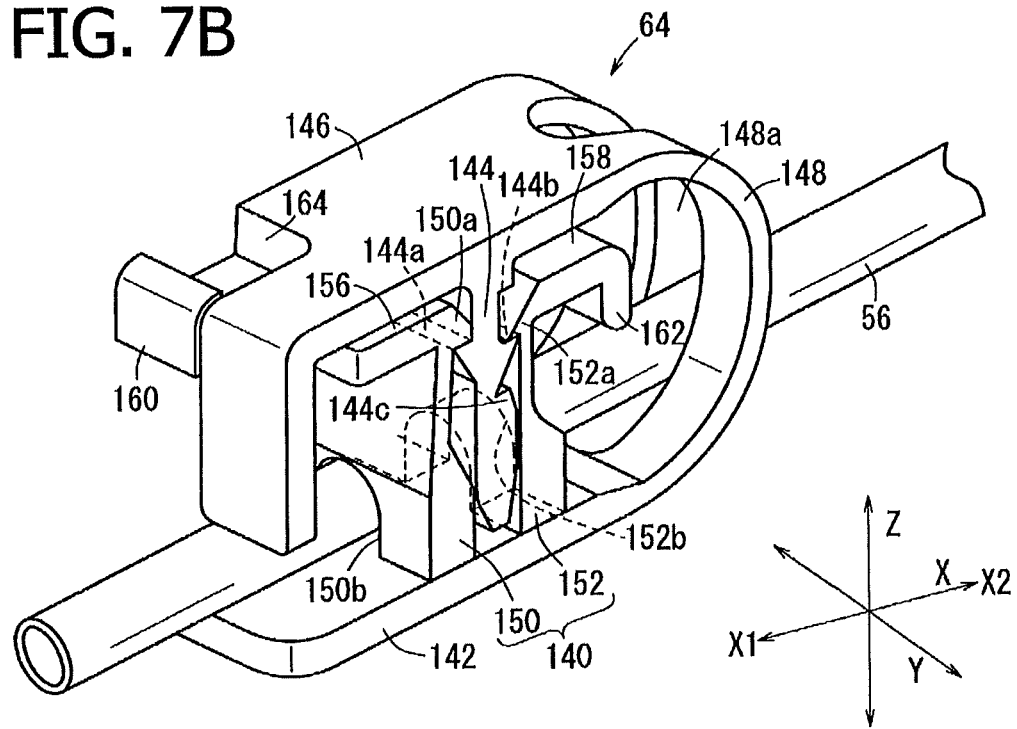
FIG. 7B is a perspective view of a condition wherein the tube is closed with the clamp.

FIGS. 7A and 7B are perspective views of the clamp 64. The clamp 64 is in a pre-locking state in FIG. 7A, and is moved to a closing state shown in FIG. 7B to close the first tube 56. As shown in FIGS. 7A and 7B, the clamp 64 includes: a base section 142 provided with a locking section 140; an opening/closing section 146 provided with a protrusion section 144; and a bent section 148 which interconnects the base section 142 and the opening/closing section 146. Thus, one end of the base section 142 and one end of the opening/closing section 146 are connected by way of the bent section 148, and the opposite ends of the base section 142 and the opening/closing section 146 are free ends. The base section 142, the opening/closing section 146 and the bent section 148 are formed integrally as a one-piece member.

The following description concerning the clamp 64, the extending direction of the base section 142 will be referred to as the X direction, the widthwise direction of the base section 142 that is orthogonal to the X direction will be referred to as the Y direction, and the direction orthogonal to both the X direction and the Y direction will be referred to as the Z direction.

The clamp 64 is composed of a resin-made member. While the base section 142, the bent section 148 and the opening/closing section 146 are shaped to be aligned on a straight line upon molding, the clamp 64 is elastically deformed so as to be bent at the portion of the bent section 148, thereby being shaped as shown in FIG. 7A or 7B.

The base section 142 is plate-shaped as a whole, and is provided with the locking section 140 at an inner surface thereof. The locking section 140 has a first engagement section or portion 150 and a second engagement section or portion 152 which both project substantially vertically (in the Z direction) from the inner surface of the base section 142. Between the first engagement section 150 and the second engagement section 152 is formed an engagement groove 154 into which the protrusion section 144 is insertable. The first engagement section 150 and the second engagement section 152 are elongated members integrally formed in one piece with the base section 142, and projecting away from the base section 142 toward the opening/closing section 146. The first engagement section 150 and the second engagement section 152 are formed at their tips with engagement claws 150a, 152a which project toward the engagement groove 154 side, and in a direction towards each other, and are engageable with the protrusion section 144.

The first engagement section 150 and the second engagement section 152 are provided in their base portions with through-holes 150b, 152b which are bored along the extending direction (X direction) of the base section 142 and are so sized that the first tube 56 can be inserted though the through-holes 150b, 152b. In addition, the bent section 148 is provided with a through-hole 148a which extends along the extending direction of the bent section 148, penetrates the bent section 148 in the thickness direction of the bent section 148, and is so sized that the first tube 56 can be inserted through the through-hole 148a.

To the first engagement section 150 is connected a base portion of a first engagement release section 156. The first engagement release section 156 in the configuration shown by way of example bends from the tip of the first engagement section 150 and extends in such a direction as to extend away from the second engagement section 152. In an engaged state between the protrusion section 144 and the locking section 140, the first engagement release section 156 is located between the base section 142 and the opening/closing section 146. At the tip of the first engagement release section 156 is provided a first hook piece 160 which is bent outward and is engageable with the second pressing element 134 of the clamp operating section 124. The first engagement release section 156 may be provided at s position other than the tip of the first engagement section 150 such as at an intermediate position in the extending direction (Z direction) of the first engagement section 150.

The second engagement section 152 is connected to the base of the second engagement release section 158. The second engagement release section 158 according to the configuration shown by way of example bends from the tip of the second engagement section 152 and extends toward the bent section 148 side. In addition, the tip of the second engagement release section 158 is provided with a second hook piece 162 engageable with a release pin 166 (see FIG. 8) for putting (holding) the second engagement release section 158 in a releasing state. The second hook piece 162 in the example shown is bent to the Z2 direction side at a tip portion of the second engagement release section 158. The second engagement release section 158 may be provided at a position other than at the tip of the second engagement section 152 such as at an intermediate position in the extending direction (Z direction) of the second engagement section 152.

The opening/closing section 146 is plate-shaped as a whole, and the protrusion section 144 for pressing the first tube 56 is provided roughly vertically at an inner surface of the opening/closing section 146. The protrusion section 144 is an elongated member integrally formed in one piece with the opening/closing section 146, and projecting away from the opening/closing section 146 toward the base section 142. In addition, the opening/closing section 146 is provided with an opening section 164 for partly exposing the first engagement release section 156 so as to be capable of pressing the first engagement release section 156 from outside. The opening section 164 according to the configuration shown by way of example is a cutout provided on one side, in the width-direction (X-direction) of the opening/closing section 146, but the opening section is not limited in this regard. The opening section 164 may be formed as an opening which penetrates the opening/closing section 146 in the thickness direction (Y direction) of the latter.

The protrusion section 144 is provided at its one side surface with a claw section (claw) 144a engageable with the engagement claw 150a of the first engagement section 150. The protrusion section 144 is provided at its other side surface with two claw sections (claws) 144b, 144c each engageable with the engagement claw 152a of the second engagement section 152.

The claw section 144c is provided on the side of the tip of the protrusion section 144 relative to the claw section 144b. When the engagement claw 152a of the second engagement section 152 is engaged with the claw section 144c, as shown in FIG. 7A, the first tube 56 is in a pre-locked state in which the first tube 56 is insertable through the through-holes 150b, 152b. In this pre-locked state, therefore, the first tube 56 is not pressed by the protrusion section 144, and the flow path in the first tube 56 is in an open state.

When the protrusion section 144 is inserted into the engagement groove 154 to such a position that the engagement claws 150a, 152a of the first engagement section 150 and the second engagement section 152 are respectively engaged with the claw sections 144a, 144b of the protrusion section 144, as shown in FIG. 7B, the first tube 56 is pressed by the protrusion section 144 and the flow path in the first tube 56 is closed.

Figure 8:
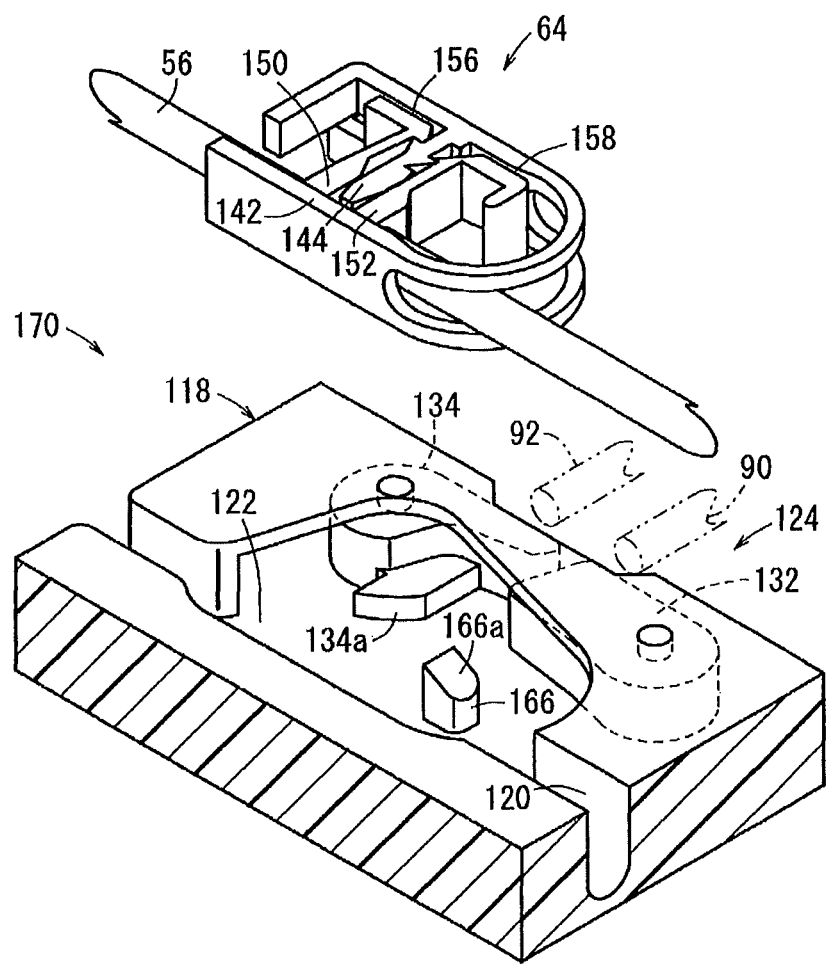
FIG. 8 is a perspective view of a clamp opening and closing mechanism.

FIG. 8 is a partly omitted schematic perspective view showing the configuration of a clamp opening and closing mechanism 170 provided in the tube holder 118. The clamp opening and closing mechanism 170 includes a clamp holding section 122 for holding and positioning the clamp 64, the release pin 166 provided on the clamp holding section 122, and a clamp operating section 124 for operations of opening and closing the clamp 64.

The release pin 166 is a member which projects upward from a bottom surface of the clamp holding section 122 and is formed with a taper surface 166a at its tip portion. The release pin 166 presses the second engagement release section 158 of the clamp 64 mounted to the clamp holding section 122 in a lateral direction (B2 direction), thereby displacing the second engagement section 152 to an engagement released position.

The clamp operating section 124 has the first pressing element 132 and the second pressing element 134, as described above. The first pressing element 132 is swung (moved or rotated) by operation of the first rod 90 to press the opening/closing section 146 inward; on the other hand, the second pressing element 134 is swung (moved or rotated) by operation of the second rod 92 to incline the first engagement release section 156. The first pressing element 132 and the second pressing element 134 are rotatably supported on the tube holder 118 through the pins 128, 130, respectively, and are biased in the A2 direction by springs. When pressed by the first rod 90 and the second rod 92, the first pressing element 132 and the second pressing element 134 are displaced or moved (rotated) toward the clamp holding section 122 side (in the A1 direction) against biasing forces of the springs.

FIGS. 9A-9C are schematic operation illustrations showing the manner in which the clamp 64 is opened by the clamp opening and closing mechanism 170. When the clamp 64 is mounted to the clamp holding section 122 as shown in FIG. 9A, the second engagement release section 158 of the clamp is pressed by the release pin 166, and the second engagement section 152 is elastically deformed and displaced in the B2 direction. In this case, the second engagement release section 158 is guided by the taper surface 166a provided at an upper portion of the release pin 166, so that the mounting of the clamp 64 to the clamp holding section 122 can be carried out rather smoothly.

With the second engagement section 152 thus displaced in the B2 direction, the engagement claw 152a of the second engagement section 152 is released from the claw section 144b of the protrusion section 144, and the second engagement section 152 is put into an engagement released state. Therefore, in the condition where the clamp 64 is mounted to the clamp holding section 122, the second engagement section 152 of the clamp 64 is always in the engagement released state.

When the second rod 92 is advanced, as shown in FIG. 9B, the second pressing element 134 is turned, and the release claw 134a provided as part of the second pressing element 134 is hooked on or presses on the first hook piece 160 of the first engagement release section 156, whereby the first engagement section 150 is elastically deformed and displaced in the B1 direction. As a result, the engagement claw 150a of the first engagement section 150 is released from the claw section 144a of the protrusion section 144, and the first engagement section 150 is put into a disengaged state.

Thus, with both the first engagement section 150 and the second engagement section 152 put into the engagement released state, the locking of the protrusion section 144 by the locking section 140 is released; therefore, the protrusion section 144 is displaced in the A2 direction, as shown in FIG. 9C. As a result, the clamp 64 is put into an opened state, and the flow path in the first tube 56 is opened.

Figure 10A:
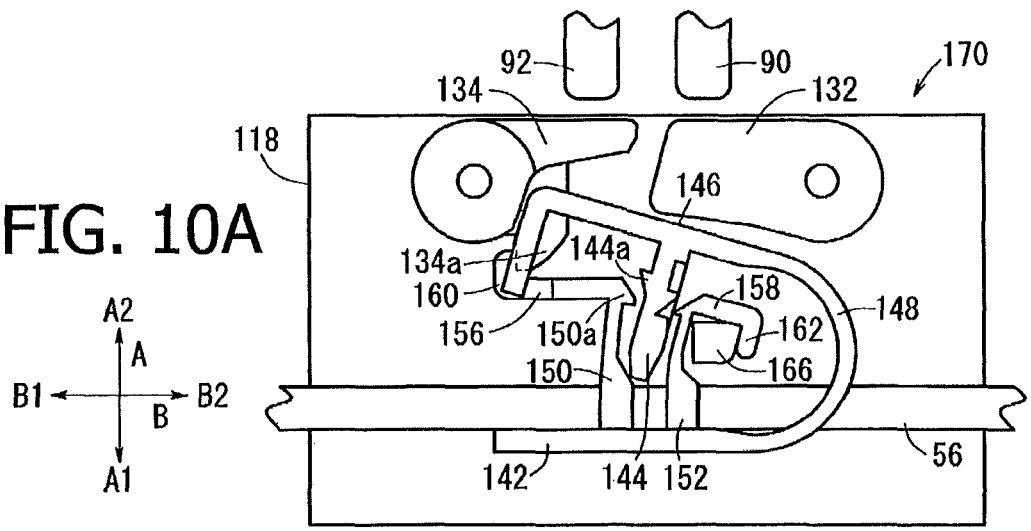
FIG. 10A is a view showing a condition in which the first engagement section has returned into an original position thereof.
Figure 10B:
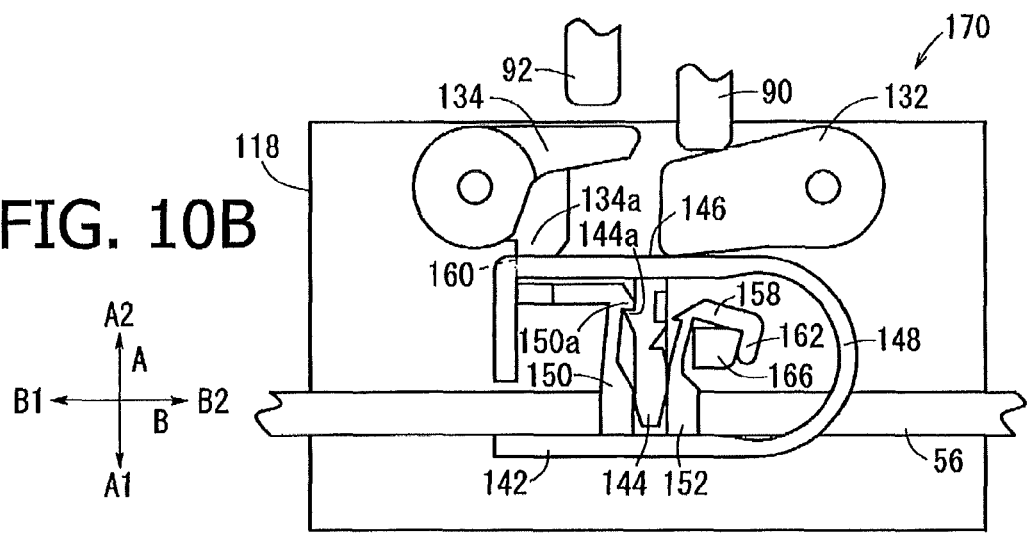
FIG. 10B is a view showing a condition wherein an opening/closing section is pressed to engage the first engagement section with the protrusion section.
Figure 10C:
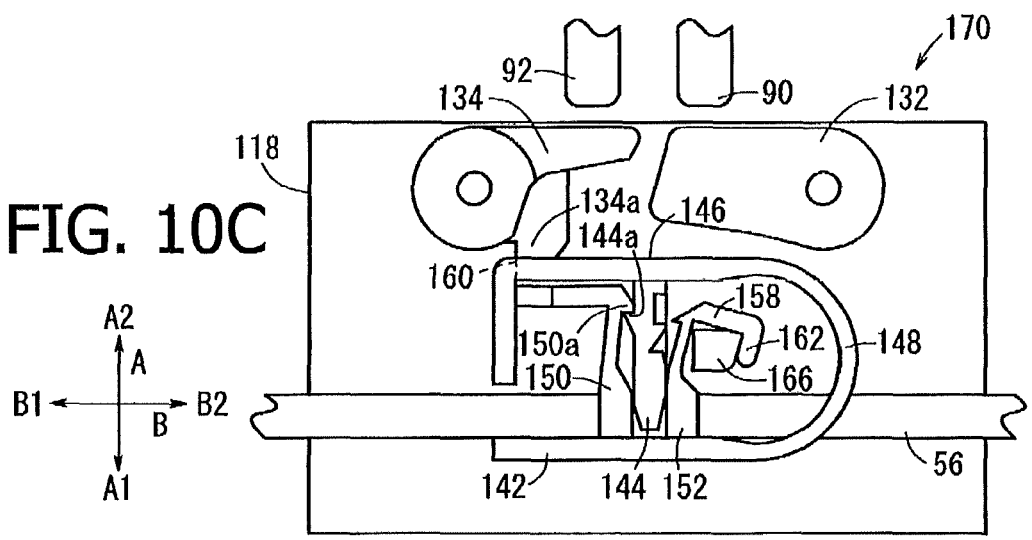
FIG. 10C is a view showing a condition wherein the tube is closed by pressing the protrusion section.

FIGS. 10A-10C are schematic operation illustrations showing the manner in which the clamp 64 is opened by the clamp opening and closing mechanism 170. When the second rod 92 is retracted, as shown in FIG. 10A, the second pressing element 134 is returned into its original position, and the first engagement release section 156 is also returned in its original position. When the first rod 90 is advanced, starting from this condition, the first pressing element 132 is turned to press the opening/closing section 146 of the clamp 64 in the A1 direction.

As a result, the protrusion section 144 is inserted to a deep position in the engagement groove 154, and the engagement claw 150a of the first engagement section 150 is engaged with the claw section 144a of the protrusion section 144, whereby the protrusion section 144 is locked by the first engagement section 150. This helps ensure that as shown in FIG. 10C, the clamp 64 is closed, and the first tube 56 is pressed by the protrusion section 144, whereby the flow path in the first tube 56 is closed.

As described above, according to the clamp 64 in this embodiment, the locking of the protrusion section 144 by the locking section 140 is not released unless both the engagement of the first engagement release section 156 and the engagement of the second engagement release section 158 are released. Therefore, the closed state of the first tube 56 can be maintained relatively assuredly and stably.

Since the second engagement release section 158 is provided between the protrusion section 144 and the bent section 148, it is difficult to operate by the fingers of the person who handles the clamp 64. With the second engagement release section 158 thus located in a position where it is difficult to operate, the closed state of the first tube 56 can be maintained further assuredly.

In the clamp 64 according to this embodiment, the second engagement release section 158 is put into an engagement releasing state by engagement of the second hook piece 162 with the release pin 166. Therefore, the second engagement release section 158 can be relatively smoothly put into the engagement releasing state by an action of the second hook piece 162.

The first engagement release section 156 is bent from the tip of the first engagement section 150 and extends in such a direction as to extend away from the second engagement section 152. In addition, in the engaged state of the protrusion section 144 and the locking section 140, the first engagement release section 156 is located between the base section 142 and the opening/closing section 146; therefore, it is difficult to operate by the fingers of the person who handles the clamp 64. With the first engagement release section 156 thus located in a position where it is difficult to operate, the closed state of the first tube 56 can be maintained more reliably.

The opening/closing section 146 is provided with the opening section 164 which enables the first engagement release section 156 to be pressed from outside. Therefore, the first engagement release section 156 can be pressed from outside of the opening/closing section 146 through the opening section 164. Accordingly, even in the case where means for operating the first engagement release section 156 is provided at a position outside of the first engagement release section 156, the first engagement release section 156 can be relatively easily put into the releasing state.

In addition, according to the blood bag system 10 in this embodiment, the clamp 64, which can be stably maintained in a locked state and can be opened when necessary, is attached to the first tube 56. Therefore, it is possible, by opening and closing the flow path in the first tube 56, to switch the communication condition between the primary bag 50 and the sub bag 52, and thereby to suitably carry out desired blood treatments.

Figure 11:
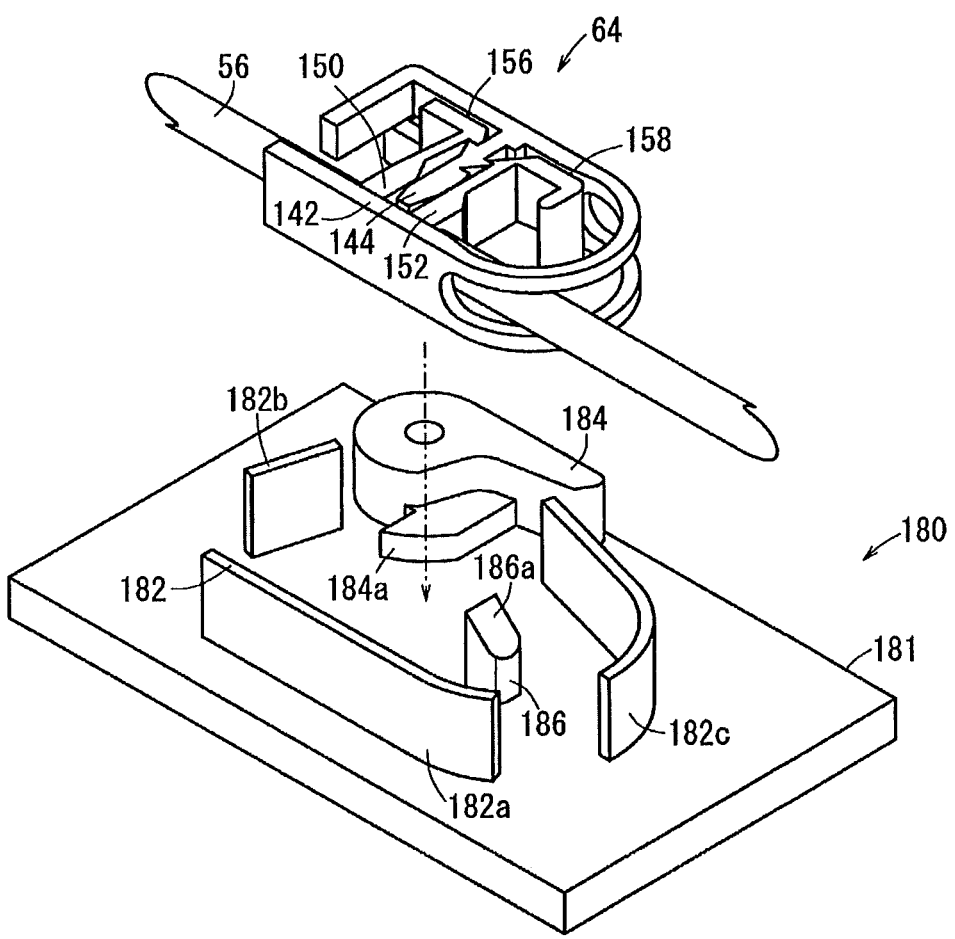
FIG. 11 is a perspective view of a clamp opening jig.

The clamp 64 can be opened/closed not only by the clamp opening and closing mechanism 170 provided in the tube holder 118 as above-described, but also by use of a clamp opening jig 180 as shown in FIG. 11. The clamp opening jig 180 includes a base plate 181, a clamp holding section 182 for positioning and fixing the clamp 64, a pressing element 184 for pressing the first engagement release section 156, and a release pin 186 for pressing the second engagement release section 158.

The clamp holding section 182 in the clamp opening jig 180 has a function of mounting the clamp 64 and fixing the clamp 64 so as to prevent the clamp 64 from moving out of position, like the clamp holding section 122 in the clamp opening and closing mechanism 170. The clamp holding section 182 according to one configuration disclosed by way of example is composed of three wall portions 182a, 182b, 182c projecting from the base plate 181; however, the clamp holding section may be composed of a groove or grooves opening to the upper side, like the clamp holding section 122. In the embodiment shown in FIG. 11, the wall portions 182a, 182b, 182c together define an upstanding wall that surrounds the clamp holding section 182, similar to the wall surrounding the recessed region or groove forming the clamp holding section 122 described above.

The release pin 186 is configured in the same manner as the release pin 166 in the clamp opening and closing mechanism 170. The pressing element 184 is configured in the same manner as the second pressing element 134 in the clamp opening and closing mechanism 170, and has a release claw 184a configured in the same manner as the release claw 134a.

When the clamp 64 is mounted to such a clamp opening jig 180, the second engagement release section 158 is pressed by the release pin 186, whereby the second engagement section 152 is put into a disengaged state. When the pressing element 184 is then pressed by a finger, the first engagement release section 156 is pressed by the release claw 184a, whereby the first engagement section 150 is put into a disengaged state, and the clamp 64 is opened. In other words, by using the clamp opening jig 180 it is possible to open the clamp 64, without need to mount the clamp 64 to the tube holder 118. Therefore, even in the case where it becomes necessary, for some reason, to open the clamp 64 at a stage prior to mounting the clamp 64 to the tube holder 118, the clamp 64 can be opened relatively easily and speedily without any needless operation.

While the clamp 64 is provided on the tube (first tube 56) in a multiple bag system (separating treatment section 16) inclusive of the primary bag 50, the sub bag 52 and the additive solution bag 54 in this embodiment, the clamp 64 may be provided on a tube in a blood bag system 10 having other forms or arrangements. Accordingly, the clamp 64 may be provided, for example, a tube in a blood bag system used for separating whole blood into three components including plasma, buffy coat and concentrated red blood cells.

In addition, the clamp 64 disclosed here may be used as the clamps 30, 36, 48. The clamp 64 may also be provided on the second tube 58 and on the third tube 60.

The detailed description above describes a clamp which closes and opens a flow path in a tube, a blood bag system embodying the clamp and a method of using the clamps. But the invention here is not limited to the precise embodiments and variations described above and illustrated in the drawing figures. Various changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A blood bag system comprising:
a plurality of bags each configured to contain whole blood or a blood component;
at least one tube interconnecting the plurality of bags;
a clamp attached to the tube;
the clamp comprising;
a protrusion section configured to press the tube;
a locking section having a first engagement portion configured to engage the protrusion section, a second engagement portion configured to engage the protrusion section, and an engagement groove located between the first engagement portion and the second engagement portion to receive the protrusion section;
a first engagement release section configured so that, when the first engagement release section is operated, the first engagement release section moves the first engagement portion out of engagement with the protrusion section to release an engaged state between the first engagement portion and the protrusion section;
a second engagement release section which releases an engaged state between the second engagement portion and the protrusion section; and
the protrusion section being movable from a position in which the first engagement portion is in the engaged state with respect to the protrusion section so that the protrusion section is maintained at a position in contact with the tube to close a flow path through the tube, to a different position in which the engaged states of both the first engagement portion and the second engagement portion are released so that the protrusion section is spaced from the tube to open the flow path through the tube.

2. The blood bag system according to claim 1, wherein the protrusion section is an elongated member that includes a plurality of spaced apart claws, the elongated member being positioned between the first engagement portion and the second engagement portion, the first engagement portion includes an engagement claw which engages a first one of the claws of the elongated member in the engaged state of the first engagement portion to maintain the elongated member at the position in contact with the tube so that the tube is closed, and the second engagement portion including an engagement claw which engages a second of the claws of the elongated member in an engaged state of the second engagement portion.

3. The blood bag system according to claim 1, wherein the first engagement portion includes a first bore through which passes the tube and the second engagement portion includes a second bore through which passes the tube, the first bore being different from and spaced apart from the second bore.

4. The blood bag system according to claim 1, wherein the clamp comprises a base section having a free end, an opening/closing section having a free end, and a bent section that is curved and connects the base section and the opening/closing section to one another so that the base section and the opening/closing section are positioned in opposing spaced apart relation to one another, the base section, the opening/closing, section and the bent section being integrally formed in one piece, the bent section including a through hole through which the tube passes.

5. The blood bag system according to Claim 4, wherein:
the protrusion section is integrally formed in one piece with the opening/closing section and projects toward the base section;
the first engagement portion is integrally formed in one piece with the base section and projects toward the opening/closing section;
the second engagement portion is integrally formed in one piece with the base section and projects toward the opening/closing section;
the first and second engagement portions are spaced apart from one another so that an engagement groove exists between the first and second engagement portions; and
the protrusion section is positioned in the engagement groove between the first engagement portion and the second engagement portion, the protrusion section having one surface facing in one direction and an opposite surface facing in a direction opposite the one direction, the one surface of the protrusion section facing a surface of the first engagement portion, the opposite surface of the protrusion section facing a surface of the second engagement portion, the one surface of the protrusion section including a claw that engages an engagement claw on the surface of the first engagement portion when the first engagement portion is in the engaged state with respect to the protrusion section.

6. A blood bag system comprising:
a first bag configured to contain a blood component;
a second bag configured to contain a supernatant component obtained by centrifugation of the blood component;
a third bag configured to contain a preservation liquid for preservation of a precipitated component obtained by centrifugation of the blood component;
a transfer line interconnecting the first bag and the second bag, and interconnecting the first bag and the third bag, and having a branching section at an intermediate position of the transfer line;
a clamp attached to the transfer line at a position between the first bag and the branching section of the transfer line;
the clamp comprising
a protrusion section configured to press the transfer line;
a locking section having a first engagement portion configured to engage the protrusion section, a second engagement portion configured to engage the protrusion section, and an engagement groove located between the first engagement portion and the second engagement portion to receive the protrusion section;
a first engagement release section configured so that, when the first engagement release section is operated, the first engagement release section moves the first engagement portion out of engagement with the protrusion section to release an engaged state between the first engagement portion and the protrusion section;
a second engagement release section which releases an engaged state between the second engagement portion and the protrusion section; and
the protrusion section being movable from a position in which the first engagement portion is in the engaged state with respect to the protrusion section so that the protrusion section is maintained at a position in contact with the transfer line to close a flow path through the transfer line, to a different position in which the engaged states of both the first engagement portion and the second engagement portion are released so that the protrusion section is spaced from the transfer line to open the flow path through the transfer line.

7. The blood bag system according to claim 6, wherein the protrusion section is an elongated member that includes a plurality of spaced apart claws, the elongated member being positioned between the first engagement portion and the second engagement portion, the first engagement portion includes an engagement claw which engages a first one of the claws of the elongated member in the engaged state of the first engagement portion to maintain the elongated member at the position in contact with the tube so that the tube is closed, and the second engagement portion including an engagement claw which engages a second of the claws of the elongated member in an engaged state of the second engagement portion.

8. The blood bag system according to claim 6, wherein the first engagement portion includes a first bore through which passes the tube and the second engagement portion includes a second bore through which passes the tube, the first bore being different from and spaced apart from the second bore.

9. The blood bag system according to claim 6, wherein the clamp comprises a base section having a free end, an opening/closing section having a free end, and a bent section that is curved and connects the base section and the opening/closing section to one another so that the base section and the opening/closing section are positioned in opposing spaced apart relation to one another, the base section, the opening/closing section and the bent section being integrally formed in one piece, the bent section including a through hole through which the tube passes.

10. The blood bag system according to claim 9, wherein:
the protrusion section is an elongated member integrally formed in one piece with the opening/closing section and projects toward the base section;
the first engagement portion is integrally formed in one piece with the base section and projects toward the opening/closing section;
the second engagement portion is integrally formed in one piece with the base section and projects toward the opening/closing section;
the first and second engagement portions are spaced apart from one another so that an engagement groove exists between the first and second engagement portions; and
the elongated member is positioned in the engagement groove between the first engagement portion and the second engagement portion, the elongated member having one surface facing in one direction and an opposite surface facing in a direction opposite the one direction, the one surface of the elongated member facing a surface of the first engagement portion and the opposite surface of the elongated member facing a surface of the second engagement portion, the one surface of the elongated member including a claw projecting toward the surface of the first engagement portion, the surface of the first engagement portion including an engagement claw projecting toward the one surface of the elongated member, the a claw on the one surface of the elongated member engages the engagement claw on the surface of the first engagement portion when the first engagement portion is in the engaged state with respect to the elongated member.

11. A blood bag system comprising:
a plurality of bags each having an interior configured to contain whole blood or a blood component;

a tube connecting the interior of one of the bags to the interior of an other of the bags;

a clamp attached to the tube;

a tube holder comprised of a tube guide passage in which at least a portion of the tube is positioned and a clamp holder located at intermediate portion of the tube guide passage, the clamp being positioned in the clamp holder;

the clamp which is positioned in the clamp holder comprising;

an elongated protrusion section movable into contact with the tube to close a flow passage in the tube and movable away from the tube to open the flow passage;

an elongated first engagement portion engageable with one part of the protrusion section in an engaged state of the first engagement portion to hold the protrusion section at a position at which the protrusion section is in contact with the tube and closes the flow passage in the tube, the first engagement portion being movable from the engaged state to a disengaged state of the first engagement portion in which the first engagement portion is out of engagement with the one part of the protrusion section;

a first engagement release section configured so that, when the first engagement release section is operated, the first engagement release section moves the first engagement portion out of engagement with the protrusion section to release the engaged state between the first engagement portion and the one part of the protrusion section to move the first engagement portion to the disengaged state of the first engagement portion; and the protrusion section being held in contact with the tube to close the flow passage in the tube in the engaged state of the first engagement portion and being movable out of contact with the tube to open the flow passage when the first engagement portion is in the disengaged state.

12. The blood bag system according to claim 11, wherein the clamp further comprises: a second engagement portion engageable with an other part of the protrusion section in an engaged state of the second engagement portion, the second engagement portion being movable from the engaged state of the second engagement portion to a disengaged state of the second engagement portion in which the second engagement portion is out of engagement with the other part of the protrusion section; and a second engagement release section which releases the engaged state between the second engagement portion and the other part of the protrusion section to move the second engagement portion to the disengaged state of the second engagement portion.

13. The blood bag system according to claim 11, wherein the clamp comprises a base section, an opening/closing section, and a bent section connecting the base section and the opening/closing section to one another so that the base section and the opening/closing section are positioned in opposing spaced apart relation to one another, the tube holder further comprising a rotatably mounted pressing element which is rotatable into contact with the opening/closing section to move the first engagement portion into the engaged state, the pressing element being separate from the clamp and being rotatable about an axis spaced from the clamp.

14. The blood bag system according to claim 11, wherein the tube holder further comprises a rotatably mounted pressing element configured to contact the first engagement release section upon rotation of the pressing element to release the engaged state between the first engagement portion and the one part of the protrusion section, the pressing element being separate from the clamp and being rotatable about an axis spaced from the clamp.

15. A clamp for closing and opening a flow path in a tube, comprising:

a protrusion section configured to press the tube;

a locking section having a first engagement portion configured to engage a first part of the protrusion section, a second engagement portion configured to engage a second part of the protrusion section different from and spaced apart from the first part of the protrusion section, and an engagement groove located between the first engagement portion and the second engagement portion to receive the protrusion section;

the first engagement portion being in direct contacting engagement with the first part of the protrusion section in an engaged state between the first engagement portion and the first part of the protrusion section to hold the protrusion section in a position pressing against and closing a flow path through the tube;

the second engagement portion being configured to be in direct contacting engagement with the first part of the protrusion section in an engaged state between the second engagement portion and the second part of the protrusion section;

a first engagement release section configured so that, when the first engagement release section is operated, the first engagement release section moves the first engagement portion out of engagement with the protrusion section to release the engaged state between the first engagement portion and the first part of the protrusion section;

a second engagement release section which releases the engaged state between the second engagement portion and the second part of the protrusion section; and the protrusion section being movable from a position in which the first engagement portion is in the engaged state with respect to the first part of the protrusion section so that the protrusion section is maintained at a position in contact with the tube to close the flow path through the tube, to a different position in which the engaged states of both the first engagement portion and the second engagement portion are released so that the protrusion section is spaced from the tube to open the flow path through the tube.

16. The clamp according to claim 15, wherein:

the clamp comprises a base section having a free end, an opening/closing section having a free end, and a bent section connecting the base section and the opening/closing section so that the base section and the opening/closing section are positioned in opposing spaced apart relation to one another;

the locking section is a part of the base section, and the protrusion section is a part of the opening/closing section;

the base section, the opening/closing section and the bent section are integrally formed in one piece;

the first engagement portion and the second engagement portion are spaced apart from one another in a direction from a free end of the base section toward the bent section, with the second engagement portion being located closer to the bent section that the first engagement portion; and the second engagement release section is located between the protrusion section and the bent section in a condition where the protrusion section and the locking section are engaged with each other.

17. The clamp according to claim 16, wherein the second engagement release section projects from the second engagement portion toward the bent section; and further comprising a hook piece at a tip of the second engagement release section, the hook piece being engageable with a release pin for positioning the second engagement release section in a releasing state in which the engaged state of the second engagement portion is released.

18. The clamp according to claim 16, wherein the first engagement release section projects from the first engagement section in a direction away from the second engagement section, the first engagement release section being located between the base section and the opening/closing section when the protrusion section and the locking section are engaged with each other.

19. The clamp according to claim 18, wherein the opening/closing section includes a through opening which partly exposes the first engagement release section so that the first engagement release section is pressable from outside the opening/closing section by way of the through opening.

20. The clamp according to claim 15, further comprising:
a first plate-shaped member connected to and spaced apart from a second plate-shaped member so that the first plate-shaped member and the second plate-shaped member are relatively movable;
the protrusion section is an elongated protrusion section fixed to the first plate-shaped member, projecting away from the first plate-shaped member and projecting toward the second plate-shaped member;
the first engagement portion is an elongated first engagement portion fixed to the second plate-shaped member, projecting away from the second plate-shaped member and projecting toward the first plate-shaped member;
the second engagement portion is an elongated second engagement portion fixed to the second plate-shaped member, projecting away from the second plate-shaped member and projecting toward the first plate-shaped member; and
the elongated first engagement portion and the elongated second engagement portion being spaced apart from one another so that an engagement groove exists between the elongated first engagement portion and the elongated second engagement portion, the elongated protrusion section being positioned in the engagement groove.

21. The clamp according to claim 15, further comprising:
a first plate-shaped member, a second plate-shaped member, and a connecting member directly connected to one end of the first plate-shaped member and one end of the second plate-shaped member, the connecting portion allowing relative movement between the first part and the second part;
the first engagement portion, the second engagement portion and the connecting member each including a respective through hole; and
the through hole in the connecting member, the through hole in the first engagement portion and the through hole in the second engagement portion being aligned with one another to allow the tube to pass through the through hole in the connecting member, the through hole in the first engagement portion and the though hole in the second engagement portion.

* * * * *